United States Patent [19]

Imashiro et al.

[11] Patent Number: 5,488,170
[45] Date of Patent: Jan. 30, 1996

[54] PROCESS FOR PRODUCING 3-METHYL-1-PHENYLPHOSPHOLENE OXIDE

[75] Inventors: Yasuo Imashiro; Naofumi Horie; Takeshi Yamane, all of Tokyo, Japan

[73] Assignee: Nisshinbo Industries, Inc., Tokyo, Japan

[21] Appl. No.: 266,552

[22] Filed: Jun. 28, 1994

[30] Foreign Application Priority Data

Jul. 2, 1993 [JP] Japan .................................. 5-190831

[51] Int. Cl.$^6$ .................................................. C07F 9/53
[52] U.S. Cl. ............................................................ 568/12
[58] Field of Search ................................................ 568/12

[56] References Cited

U.S. PATENT DOCUMENTS 2,663,737  12/1953  McCormack ............................. 568/12
3,803,225  4/1974  Smith et al. ............................. 568/12
4,080,377  3/1978  Black et al. ............................. 568/12
4,247,488  1/1981  Felcht ...................................... 568/12
4,504,683  3/1985  Breque et al. ........................... 568/12

*Primary Examiner*—James H. Reamer
*Attorney, Agent, or Firm*—Ronald J. Kubovcik

[57] ABSTRACT

A process for producing 3-methyl-1-phenylphospholene oxide by subjecting dichlorophenylphosphine and isoprene to an addition reaction and then subjecting the resulting adduct to solvolysis, wherein the addition reaction between dichlorophenylphosphine and isoprene is conducted in a solvent to obtain an adduct in the form of a slurry or solution and the slurry or solution is subjected to solvolysis.

This process can easily produce 3-methyl-1-phenylphospholene oxide which is used in various reactions, and is free from the drawbacks of the conventional process.

4 Claims, No Drawings

PROCESS FOR PRODUCING 3-METHYL-1-PHENYLPHOSPHOLENE OXIDE

BACKGROUND OF THE INVENTION

1. Field of the Invention

The present invention relates to a process for producing 3-methyl-1-phenylphospholene oxide.

2. Prior Art

Phospholene oxides having a basic structure represented by the following formula

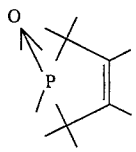

are useful compounds which are used as a catalyst in various reactions. Use of 1-phenylphospholene oxide or 3-methyl-1-phenylphospholene oxide as a catalyst effective for conversion of an organic diisocyanate into a polycarbodiimide is disclosed in Japanese Patent Application Kokai (Laid-Open) No. 348934/1992, and use of 3-methyl-1-phenylphospholene oxide as a catalyst effective for conversion of an organic diisocyanate into a polycarbodiimide is disclosed in Japanese Patent Application Kokai (Laid-Open) No. 9252/1993.

Of the phospholene oxides having the basic structure represented by the above formula, 3-methyl-1-phenylphospholene oxide

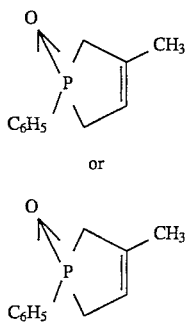

is thought to be advantageous in reactivity. The 3-methyl-1-phenylphospholene oxide having a double bond at the 3-position has been produced by a process represented by the following reaction formula, shown in Organic Synthesis.

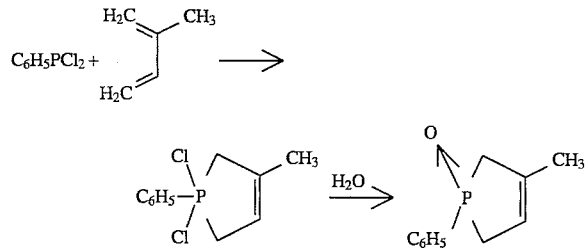

That is, said 3-methyl-1-phenylphospholene oxide has been produced by reacting dichlorophenylphosphine (1) and isoprene (2) in the presence of an antioxidant to form a solid adduct (3), hydrolyzing the adduct, neutralizing the reaction mixture, extracting the neutralized mixture with chloroform, and drying the extract and subjecting it to distillation [Organic Synthesis, 43, 73 (1963)].

The above conventional process, however, has various problems. Since isoprene (a starting material) is incorporated inside the solid adduct, the solid adduct must be ground and the ground adduct must be washed with, for example, petroleum ether for isoprene removal before the hydrolysis step; this makes the process complicated and moreover there arises the leakage of isoprene vapor during grinding and washing, deteriorating the working environment.

With respect to the above conventional process, a problem of yield is also pointed out. That is, the yield remains as low as about 57–63% even when there are used such controlled reaction conditions as (a) isoprene is used in an amount of about 3 moles per mole of dichlorophenylphosphine and (b) the reaction is conducted at room temperature for 5–7 days or even longer. The yield becomes even lower when the reaction time is shortened or the amount of isoprene is decreased.

Thus, in order to obtain 3-methyl-1-phenylphospholene oxide in an economical yield by the above-mentioned process, isoprene must be used in excess. Consequently, isoprene is incorporated inside the solid adduct. This necessitates the grinding and washing steps for the solid adduct in the actual process for production of 3-methyl-1-phenylphospholene oxide.

SUMMARY OF THE INVENTION

The present invention is intended to provide a process allowing for easy production of 3-methyl-1-phenylphospholene oxide (this compound is used in various reactions), which process is free from the drawbacks of the prior art.

According to the present invention, there is provided a process for producing 3-methyl-1-phenylphospholene oxide by subjecting dichlorophenylphosphine and isoprene to an addition reaction and then subjecting the resulting adduct to solvolysis, wherein the addition reaction between dichlorophenylphosphine and isoprene is conducted in a solvent to obtain an adduct in the form of a slurry or solution and the slurry or solution is subjected to solvolysis.

DETAILED DESCRIPTION OF THE INVENTION

The present invention is hereinafter described in detail.

The process for producing 3-methyl-1-phenylphospholene oxide according to the present invention is an improvement of the process described in the above-mentioned Organic Synthesis and is therefore basically the same as the process described in the Organic Synthesis, as is clear from the following description.

That is, also in the present process, dichlorophenylphosphine and isoprene are reacted in the presence of an antioxidant to form an adduct; the adduct is subjected to solvolysis, the reaction mixture is neutralized, the resulting mixture is extracted with an appropriate solvent, and the extract is dried and subjected to distillation; or the adduct is subjected to alcoholysis and the reaction mixture is subjected to distillation; thereby, 3-methyl-1-phenyl-phosphine oxide is obtained.

The present invention is characterized in that the reaction of dichlorophenylphosphine and isoprene in the presence of an antioxidant to form an adduct is conducted in a solvent to obtain an adduct in the form of a slurry or solution and that the slurry or solution is subjected to solvolysis. The solvent may be any solvent unless it is a highly reactive solvent, for example, an active-hydrogen-containing compound. The solvent includes, for example, organic solvents such as aromatic hydrocarbon (e.g. toluene or xylene), aliphatic hydrocarbon (e.g. hexane), halogen-containing hydrocarbon (e.g. Perclene, chloroform or methylene chloride) and nitrogen-containing hydrocarbon (e.g. N-methylpyrrolidone or pyridine).

In the present invention, the addition reaction between dichlorophenylphosphine and isoprene is conducted in a heterogeneous or homogeneous system. When the addition reaction is conducted in a heterogeneous system, neither grinding operation nor washing operation is required; it is possible to take out, from the reaction system, an adduct containing substantially no isoprene, in the form of a slurry; and the washing of the adduct, even when conducted, is easy because the adduct is a slurry. Also when the addition reaction is conducted in a homogeneous system, the resulting adduct can be used in the next step, in the form of a solution and, therefore, neither grinding operation nor washing operation is required for the adduct, as well.

Whether the addition reaction between dichlorophenylphosphine and isoprene is conducted in a heterogeneous system or in a homogeneous system, is determined depending upon the kind of the solvent used. The addition reaction is conducted in a heterogeneous system when the solvent is, for example, an aromatic hydrocarbon (e.g. toluene or xylene), an aliphatic hydrocarbon (e.g. hexane) or a halogen-containing hydrocarbon (e.g. Perclene). The addition reaction is conducted in a homogeneous system when the solvent is a halogen-containing hydrocarbon (e.g. chloroform or methylene chloride) or a nitrogen-containing hydrocarbon (e.g. N-methylpyrrolidone or pyridine).

The solvent is used in an amount of 200–400 ml per mole of dichlorophenylphosphine when the addition reaction is conducted in a heterogeneous system. The solvent is used in an amount of 100–200 ml per mole of dichlorophenylphosphine when the addition reaction is conducted in a homogeneous system. When the amount of solvent is too small, the resulting adduct becomes a solid in the heterogeneous system and, in the homogeneous system, the adduct solution has an increased viscosity, making difficult its handling. With too large a solvent amount, the addition reaction between dichlorophenylphosphine and isoprene does not proceed sufficiently.

In the present addition reaction between dichlorophenylphosphine and isoprene, unlike in the process described in Organic Synthesis, it is sufficient to use isoprene in an amount of at least 1 mole per mole of dichlorophenylphosphine and, in view of the hazard, volume, cost, etc., the amount of isoprene is preferably 1–3 moles, preferably 1–2 moles per mole of dichlorophenylphosphine. An increase in isoprene amount increases the initial rate of adduct synthesis, but makes difficult the recovery of unreacted raw material and emits an offensive odor (even a small amount emits such an odor). Hence, the isoprene amount is preferably small.

The present addition reaction between dichlorophenylphosphine and isoprene may be conducted with heating. In this case, the reaction rate is higher and the reaction time can be shortened. The heating temperature is preferably, for example, 70° C. or below in the heterogeneous system and 80° C. or below in the homogeneous system, more preferably, for example, 40°–70° C. in the heterogeneous system and 40°–80° C. in the homogeneous system. For example, when the addition reaction is conducted at 65° C. in the homogeneous system, the reaction is complete within 24 hours, and a higher reaction temperature can shorten the reaction time further. Needless to say, when the shortening of the reaction time is unnecessary, the addition reaction can be conducted, for example, at room temperature.

When sufficient stirring is conducted in the addition reaction between dichlorophenylphosphine and isoprene, the reaction rate is higher and, in the reaction in the heterogeneous system, an adduct slurry of good appearance can be obtained.

The thus obtained adduct is subjected to hydrolysis or alcoholysis and then the reaction mixture is neutralized (adjusted to pH=3–9), whereby intended 3-methyl-1-phenylphospholene oxide can be obtained. The hydrolysis can be conducted, for example, in ice water. Incidentally, said 3-methyl-1-phenylphospholene oxide is a mixture of a compound having a double bond at the 2-position and a compound having a double bond at the 3-position (the mixing ratio of the two compounds differs depending upon the reaction conditions).

The formed 3-methyl-1-phenylphospholene oxide can be isolated from the aqueous phenylphospholene oxide solution by a known operation. That is, first the aqueous phenylphospholene oxide solution is saturated with sodium chloride to carry out salting out; then, extraction is conducted using an extraction solvent such as chloroform or the like; the extract is dried as necessary and then filtered; the filtrate is concentrated to an appropriate level and then subjected to distillation; thereby, 3-methyl-1-phenylphospholene oxide is obtained as a fraction of 163–166/0.6–0.7 mmHg.

In this case, 3-methyl-1-phenyl-3-phospholene-1-oxide is obtained as an initial fraction. This oxide is 5% by weight or less of the total 3-methyl-1-phenylphospholene oxide obtained in the present process.

When the above hydrolysis is replaced by alcoholysis, the above steps of neutralization, salting out, extraction and drying can be omitted.

The present invention is hereinafter described in more detail by way of Examples.

Examples of production in heterogeneous system

Example 1

In a 1-liter autoclave were placed 179 g (1 mole) of dichlorophenylphosphine, 204 g (3 moles) of isoprene, 3 g of an antioxidant [Ionol (trade mark)] (the same antioxidant was used in the following Examples) and 400 ml of toluene as a solvent. They were stirred at 70° C. for 24 hours to give rise to a reaction.

After the completion of the reaction, the reaction mixture was cooled to room temperature and filtered to separate the precipitated adduct. The adduct was sufficiently washed with toluene and then added to 700 ml of water to conduct hydrolysis. The hydrolysis mixture was adjusted to about pH 6.5 with a 48% aqueous sodium hydroxide solution. Thereto was added sodium chloride until it became saturated.

The above mixture was extracted with chloroform. The extract containing the reaction product formed above was dehydrated and then subjected to distillation to remove chloroform. The residual liquid was subjected to vacuum distillation to obtain 147 g (77% of theoretical yield) of 3-methyl-1-phenyl-2-phospholene-1-oxide.

Examples 2–4

Reactions were conducted under the same conditions as in Example 1, with the reaction temperatures and reaction times varied. The results are shown in Table 1. In Table 1, DCPP and Isop refer to dichlorophenylphosphine and isoprene, respectively (the same applies to the following Examples).

TABLE 1

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 2 | 1 | 3 | Toluene | 400 | 30 | 336 | 73 |
| Ex. 3 | 1 | 3 | Toluene | 400 | 50 | 72 | 75 |
| Ex. 4 | 1 | 3 | Toluene | 400 | 65 | 67 | 78 |

As is clear from Table 1, the reaction time is shorter as the reaction temperature is higher, and the intended substance could be obtained in a high yield in all cases. Incidentally, when the reaction time was higher than 70° C. by a large margin, the amount of impurities (distillation residue) was large; the adduct was not in the form of a slurry; and by-products were formed.

Examples 5–10

Reactions were conducted under the same conditions as in Example 1, with the amount of isoprene varied. The results are shown in Table 2.

TABLE 2

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 5 | 1 | 1.0 | Toluene | 400 | 65 | 24 | 59 |
| Ex. 6 | 1 | 1.2 | Toluene | 400 | 65 | 24 | 66 |
| Ex. 7 | 1 | 1.5 | Toluene | 400 | 65 | 24 | 68 |
| Ex. 8 | 1 | 2 | Toluene | 400 | 65 | 24 | 69 |
| Ex. 9 | 1 | 3 | Toluene | 400 | 65 | 24 | 75 |
| Ex. 10 | 1 | 5 | Toluene | 400 | 65 | 24 | 70 |

As is clear from Table 2, the intended substance could be obtained in a high yield even when isoprene was used in an amount equimolar to dichlorophenylphosphine, and an increase in yield could be seen when isoprene was used in excess. However, use of isoprene in an amount exceeding 3 moles showed no further increase in yield. Hence, the amount of isoprene used is preferably 1-3 moles. Since the reaction is a 1:1 addition reaction, use of isoprene in an amount of less than 1 mole is not preferable.

Examples 11–12 and Comparative Examples 1–2

Reactions were conducted under the same conditions as in Example 1, with the amount of solvent varied. The results are shown in Table 3.

TABLE 3

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 11 | 1 | 3 | Toluene | 200 | 70 | 24 | 68 |
| Ex. 12 | 1 | 3 | Toluene | 400 | 70 | 24 | 77 |
| Comp. Ex. 1 | 1 | 3 | Toluene | 100 | 70 | 24 | 60 |
| Comp. Ex. 2 | 1 | 3 | Toluene | 600 | 70 | 24 | 59 |

In Comparative Example 1, the adduct solidified. In Comparative Example 2, the reaction was not complete. Since use of the solvent in an amount more than necessary results in a reduction in productivity, it is preferable to use, under the above reaction conditions, the solvent of 200–400 ml per mole of dichlorophenylphosphine.

Examples 13–14

Reactions were conducted under the same conditions as in Example 1, with the kind of solvent varied. The results are shown in Table 4.

TABLE 4

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 13 | 1 | 3 | Perclene | 400 | 65 | 24 | 66 |
| Ex. 14 | 1 | 3 | Hexane | 400 | 65 | 24 | 58 |

It is known that there can also be used other solvents such as benzene types (e.g. benzene, xylene, chlorobenzene and dichlorobenzene), ether types (e.g. diethyl ether and THF), halogen-containing hydrocarbon types (e.g. 1,2-dichloroethane, 1,1,1-trichloroethane and chlorobutane), hydrocarbon types (e.g. acetone and cyclohexane) and the like.

Example 15

In a 1-liter autoclave were placed 179 g (1 mole) of dichlorophenylphosphine, 82 g (1.2 moles) of isoprene, 3 g of an antioxidant and 400 ml of toluene (solvent). They were stirred at 65° C. for 24 hours to give rise to a reaction.

After the completion of the reaction, the reaction mixture was cooled to room temperature. The precipitated adduct was separated by filtration, then washed with toluene sufficiently, and added to 700 ml of methanol to conduct methanolysis. The reaction mixture was adjusted to about pH 6.5 with a 48% aqueous sodium hydroxide solution. The salt precipitated by this pH adjustment was removed by filtration. The filtrate (methanol solution) was subjected to distillation to remove methanol and water. The residual liquid was subjected to vacuum distillation to obtain 123 g (66% of theoretical yield) of 3-methyl- 1-phenyl-2-phospholene-1-oxide.

Example 16

In a 1-liter autoclave were placed 179 g (1 mole) of dichlorophenylphosphine, 204 g (3 moles) of isoprene, 3 g of an antioxidant and 200 ml of toluene (solvent). They were stirred at 70° C. for 24 hours to give rise to a reaction.

After the completion of the reaction, the reaction mixture was cooled to room temperature. All the reaction mixture was added to 700 ml of water to conduct hydrolysis. The reaction mixture was adjusted to about pH 6.5 with a 48% aqueous sodium hydroxide solution. Thereto was added sodium chloride until it became saturated.

The above mixture was extracted with chloroform. The extract containing a reaction product was dehydrated and then subjected to distillation to remove chloroform and toluene. The residual liquid was subjected to vacuum distillation to obtain 131 g (68% of theoretical yield) of 3-methyl-1-phenyl-2-phospholene-1-oxide.

Example 17

In a 1-liter autoclave were placed 179 g (1 mole) of dichlorophenylphosphine, 204 g (3 moles) of isoprene, 3 g of an antioxidant and 400 ml of toluene (solvent). They were stirred at 65° C. for 67 hours to give rise to a reaction.

After the completion of the reaction, the reaction mixture was cooled to room temperature. All the reaction mixture was added to 700 ml of methanol to conduct methanolysis. The reaction mixture was adjusted to about pH 6.5 with a 48% aqueous sodium hydroxide solution and then filtered to remove the salt precipitated by the pH adjustment. The filtrate was subjected to distillation to remove methanol and toluene. The residual liquid was subjected to vacuum distillation to obtain 150 g (78% of theoretical yield) of 3-methyl-1-phenyl- 2-phospholene-1-oxide.

Example 18

In a 1-liter autoclave were placed 179 g (1 mole) of dichlorophenylphosphine, 204 g (3 moles) of isoprene, 3 g of an antioxidant and 400 ml of Perclene (solvent). They were stirred at 65° C. for 24 hours to give rise to a reaction.

After the completion of the reaction, the reaction mixture was cooled to room temperature and filtered to separate the precipitated adduct. The adduct was sufficiently washed with Perclene and then added to 700 ml of water to conduct hydrolysis. The hydrolysis mixture was adjusted to about pH 6.5 with sodium hydroxide. Thereto was added sodium chloride until it became saturated.

The above mixture was extracted with chloroform. The extract containing the reaction product formed above was dehydrated and then subjected to distillation to remove chloroform and Perclene. The residual liquid was subjected to vacuum distillation to obtain 127 g (66% of theoretical yield) of 3-methyl-1-phenyl-2-phospholene-1-oxide.

Examples of production in homogeneous system

Example 19

In a 1-liter autoclave were placed 179 g (1 mole) of dichlorophenylphosphine, 120 g (1.5 moles) of isoprene, 3 g of an antioxidant and 200 ml of chloroform (solvent). They were stirred at 65° C. for 24 hours to give rise to a reaction.

After the completion of the reaction, the reaction mixture was cooled to room temperature. All the reaction mixture was added to the same volume of methanol to conduct methanolysis. The reaction mixture was adjusted to about pH 6.5 with a 48% aqueous sodium hydroxide solution and then subjected to distillation to remove chloroform, methanol and water. The residual liquid was subjected to vacuum distillation to obtain 161 g (84% of theoretical yield) of 3-methyl- 1-phenyl-2-phospholene-1-oxide.

Examples 20–22

Reactions were conducted under the same conditions as in Example 19 with the reaction temperature varied. The results are shown in Table 5.

TABLE 5

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 20 | 1 | 1.5 | Chloroform | 200 | Rm. temp. | 2 weeks | 60 |
| Ex. 21 | 1 | 1.5 | Chloroform | 200 | 45 | 67 | 65 |
| Ex. 22 | 1 | 1.5 | Chloroform | 200 | 80 | 16 | 81 |

As is clear from Table 5, as the reaction temperature was higher, the reaction time was shorter, and the intended substance could be obtained in a high yield in all cases. Incidentally, when the reaction temperature was higher than 90° C. by a large margin, the amount of distillation residue (impurities) was large and the adduct was not in the form of a slurry.

Examples 23–30

Reactions were conducted under the same conditions as in Example 19 with the amount of isoprene varied. The results are shown in Table 6.

TABLE 6

|  | DCPP (mol) | Isop (mol) | Solvent | Solvent amount (ml) | Reaction temp. (°C.) | Yield (%) 16 hr | 24 hr |
|---|---|---|---|---|---|---|---|
| Ex. 23 | 1 | 1.0 | Chloroform | 200 | 65 | 55 | 63 |
| Ex. 24 | 1 | 1.1 | Chloroform | 200 | 65 | 56 | 68 |
| Ex. 25 | 1 | 1.2 | Chloroform | 200 | 65 | 64 | 75 |
| Ex. 26 | 1 | 1.5 | Chloroform | 200 | 65 | 76 | 84 |
| Ex. 27 | 1 | 2 | Chloroform | 200 | 65 | 71 | 78 |
| Ex. 28 | 1 | 3 | Chloroform | 200 | 65 | 65 | 75 |
| Ex. 29 | 1 | 5 | Chloroform | 200 | 65 |  | 63 |
| Ex. 30 | 1 | 7 | Chloroform | 200 | 65 | 65 |  |

As is clear from Table 6, the intended substance could be obtained in a high yield even when isoprene was used in an amount equimolar to dichlorophenylphosphine. Use of isoprene in an excessive amount showed an increase in yield. However, use of isoprene in an amount more than 3 moles showed no further increase in yield. Hence, the amount of isoprene used is preferably 1–3 moles. Since this reaction is a 1:1 addition reaction, use of isoprene in an amount less than 1 mole is not preferable.

Examples 31–33 and Comparative Example 3

Reactions were conducted under the same conditions as in Example 19, with the amount of solvent varied. The results are shown in Table 7.

TABLE 7

|  | DCPP (mol) | Isop (mol) | Solvent | Solvent amount (ml) | Reaction temp. (°C.) | Reaction time (hr) | Yield (%) |
|---|---|---|---|---|---|---|---|
| Ex. 31 | 1 | 1.5 | Chloroform | 100 | 65 | 24 | 68 |
| Ex. 32 | 1 | 1.5 | Chloroform | 150 | 65 | 24 | 78 |
| Ex. 33 | 1 | 1.5 | Chloroform | 200 | 65 | 24 | 84 |
| Comp. Ex. 3 | 1 | 1.5 | Chloroform | 400 | 65 | 24 | 60 |

In Comparative Example 3, the reaction was not complete. Since use of the solvent in an amount more than necessary results in reduced productivity, it is preferable to use, under the above reaction conditions, the solvent of 100–200 ml per mole of dichlorophenylphosphine.

Examples 34–36

Reactions were conducted under the same conditions as in Example 19, with the kind of solvent varied. The results are shown in Table 8.

TABLE 8

|  | Solvent | DCPP (mol) | Isop (mol) | Solvent amount (ml) | Reaction temp. (°C.) | Reaction time (hr) | Yield (%) |
|---|---|---|---|---|---|---|---|
| Ex. 34 | Methylene chloride | 1 | 3 | 200 | 65 | 12 | 49 |
| Ex. 35 | N-methyl-2-pyrrolidone | 1 | 1 | 100 | 65 | 16 | 49 |
| Ex. 36 | 1,1,2,2-tetrachloroethane | 1 | 1.5 | 200 | 65 | 16 | 65 |

Example 37

In a 1-liter autoclave were placed 179 g (1 mole) of dichlorophenylphosphine, 82 g (1.2 moles) of isoprene, 3 g of an antioxidant and 200 ml of chloroform (solvent). They were stirred at 65° C. for 24 hours to give rise to a reaction.

After the completion of the reaction, the reaction mixture was cooled to room temperature. All the reaction mixture was added to the same volume of water to conduct hydrolysis. The reaction mixture was adjusted to about pH 6.5 with a 48% aqueous sodium hydroxide solution. Thereto was added sodium chloride until it became saturated.

The above mixture was extracted with chloroform. The extract containing a reaction product was dehydrated and then subjected to distillation to remove chloroform. The residual liquid was subjected to vacuum distillation to obtain 144 g (75% of theoretical yield) of 3-methyl-1-phenyl-2-phospholene-1-oxide.

Example 38

In a 1-liter autoclave were placed 179 g (1 mole) of dichlorophenylphosphine, 204 g (3 moles) of isoprene, 3 g of an antioxidant and 200 ml of methylene chloride (solvent). They were stirred at 65° C. for 24 hours to give rise to a reaction.

After the completion of the reaction, the reaction mixture was cooled to room temperature. All the reaction mixture was added to the same volume of methanol to conduct methanolysis. The reaction mixture was adjusted to about pH 6.5 with a 48% aqueous sodium hydroxide solution and then subjected to distillation to remove methylene chloride, methanol and water. The residual liquid was subjected to vacuum distillation to obtain 94 g (49% of theoretical yield) of 3-methyl-1-phenyl-2-phospholene-1-oxide.

In the present process for producing 3-methyl-1-phenylphospholene oxide, dichlorphenylphosphine and isoprene are subjected to an addition reaction in a solvent, and the adduct obtained in a slurry or solution form is subjected to solvolysis. Therefore, 3-methyl-1-phenylphospholene oxide can be produced easily without requiring any grinding and washing steps for solid adduct which have been substantially necessary in the conventional process.

Also in the present process for producing 3-methyl-1-phenylphospholene oxide, the adduct can be taken out from the reaction system, as an intermediate of slurry or solution form. Therefore, the handling of the adduct can be made easily.

What is claimed is:

1. A process for producing 3-methyl-1-phenylphospholene oxide by subjecting dichlorophenylphosphine and isoprene to an addition reaction and then subjecting the resulting adduct to hydrolysis or alcoholysis, wherein the addition reaction between dichlorophenylphosphine and isoprene is conducted in a solvent containing no active hydrogen to obtain an adduct in the form of a slurry or solution and the slurry or solution is subjected to hydrolysis or alcoholysis, wherein isoprene is used in an amount of at least 1 mole per mole of dichlorophenylphosphine, wherein the solvent is used in an amount of 200–400 ml per mole of dichlorophenylphosphine and the addition reaction is performed at 65°–70° C. for 24 hours or less when conducted in a heterogeneous system and the solvent is used in an amount of 100–200 ml per mole of dichlorophenylphosphine and the addition reaction is performed at 65°–80° C. for 24 hours or less when conducted in a homogeneous system, and wherein said solvent is at least one member selected from the group consisting of an aromatic hydrocarbon, an aliphatic hydrocarbon, a halogen-containing hydrocarbon and a nitrogen-containing hydrocarbon.

2. A process according to claim 1, wherein isoprene is used in an amount of 1–3 moles per mole of dichlorophenylphosphine.

3. A process according to claim 1, wherein the addition reaction between dichlorophenylphosphine and isoprene is conducted in a heterogeneous system.

4. A process according to claim 1, wherein the addition reaction between dichlorophenylphosphine and isoprene is conducted in a homogeneous system.

* * * * *